US006936256B2

(12) United States Patent
Vakharia

(10) Patent No.: US 6,936,256 B2
(45) Date of Patent: Aug. 30, 2005

(54) SUB-UNIT VACCINE FOR INFECTIOUS PANCREATIC NECROSIS VIRUS

(75) Inventor: Vikram N. Vakharia, Bowie, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 0 days.

(21) Appl. No.: 10/216,981

(22) Filed: Aug. 12, 2002

(65) Prior Publication Data

US 2003/0072772 A1 Apr. 17, 2003

Related U.S. Application Data

(60) Provisional application No. 60/311,488, filed on Aug. 10, 2001.

(51) Int. Cl.$^7$ ...................... A61K 39/12; A61K 39/295; C12Q 1/70; C12N 15/09; C12P 21/02; C07K 14/005
(52) U.S. Cl. ............................... 424/204.1; 424/186.1; 424/202.1; 435/5; 435/69.1; 435/69.3; 435/69.8; 435/71.1; 530/350; 536/23.72
(58) Field of Search .......................... 435/5, 69.1, 69.3, 435/69.8, 71.1; 424/204.1, 186.1, 199.1, 202.1; 530/350; 536/23.72

(56) References Cited

U.S. PATENT DOCUMENTS

| | | | | |
|---|---|---|---|---|
| 5,165,925 A | * | 11/1992 | Leong | 424/204.1 |
| 5,788,970 A | * | 8/1998 | Vakharia et al. | 424/192.1 |
| 5,939,073 A | | 8/1999 | McLoughlin et al. | 424/204.1 |
| 6,180,614 B1 | | 1/2001 | Davis | 514/44 |
| 6,274,147 B1 | | 8/2001 | Vakharia et al. | 424/199.1 |

FOREIGN PATENT DOCUMENTS

WO  WO 99/58639  * 11/1999

OTHER PUBLICATIONS

Martin et al. DNA. 1988; 7(2): 99–106, abstract only.*
Phenix et al. Marine Biotechnology. 2000; 2: 27–37, provided in the IDS.*
Cha et al. Biotechnology Bioengineering. 1999; 65:316–324, provided in the IDS.*
McKenna et al. Marine Biotechnology. 2001; 3 (2): 103–110.*
Copy of Abstract of McKenna et al. supra showing month of publishing date obtained from springerlink.metapress.com.*
Murphy. Virus Taxonomy. In B.N. Fields et al. (ed.), Fields Virology, 3rd ed. Philadelphia: Lippencott–Raven Publishers; 1996: 39–40.*
Lipton et al. Journal of General Virology. 1984; 65 (part 6): 1095–1100, abstract only.*
Fernandez–Arias et al. Journal of General Virology. 1998; 79: 1047–1054.*
Granzow et al. Journal of Virology. 1997; 71 (11): 8879–8885.*

Belyaev, A.S. and P. Roy. 1993. Development of baculovirus triple and quadruple expression vectors: co–expression of three or four bluetongue virus proteins and the synthesis of bluetongue virus–like particles in insect cells. Nucl. Acids. Res. 21(5): 1219–1223.
Bentley, W.E., M.Y. Wang and V.N. Vakharia, 1994. Development of an efficient bioprocess for poultry vaccines using high–density insect cell culture. Ann. New York Acad. Sci. 745: 336–359.
Cha, H.J., N.G. Dalal, M.Q. Pham, V.N. Vakharia, G. Rao, W.E. Bentley. 1999. Insect larval expression process is optimized by generating fusions with green fluorescent protein. Biotechnol. Bioeng. 65:316–324.
Duncan, R. 1987. Synthesis of the infectious pancreatic necrosis virus polyprotein, detection of a virus–encoded protease, and line structure mapping of genome segment A coding regions. 3 Virology 61:3655–3664.
Leong, J.C. 1993. Viral vaccines for aquaculture. pp. 225–240 in M. Faisal and F.M. Hetrick, eds. Annual review of fish diseases. vol. 3, Pergamon Press, New York.
Maeda, S. 1989. Expression of foreign genes in insects using baculovirus vectors. Annual Review of Entomology 34:351–72.
Magyar, G. 1994. Expression of infectious pancreatic necrosis virus polyprotein and VPI in insect cells and the detection of the polyprotein in purified virus. Virology 198:437–445.
McAllister, P.E. Infectious pancreatic necrosis virus—protocol for a standard challenge to brook trout, transactions of the American Fisheries Society, 115(3): 466–470, May 1986.
McKenna, B.M. 2001. Formation of infectious pancreatic necrosis virus–like particles following expression of segment A by recombinant semliki forest virus. Marine Biotechnology 3:103–110.
Phenix, K. V. 2000. Cell culture evaluation of the semliki forest virus expression system as a novel approach for antigen delivery and expression in fish. Marine Biotechnology 2:27–37.
Saliki, J.T. 1992 Canine parvovirus empty capsids produced by expression in a baculovirus vector: use in analysis of viral properties and immunication. Journal of General Virology 73:369.
Urakawa, T.M. 1989. Synthesis of immunogenic, but non–infectious, poliovirus particles in insect cells by a baculovirus expression vector. Journal General Virology 70:1453–1463.

(Continued)

*Primary Examiner*—Shanon Foley
(74) *Attorney, Agent, or Firm*—Marianne Fuierer; Steven J. Hultquist; Yongzhi Yang

(57) ABSTRACT

The present invention relates to sub-unit vaccines comprising structural polypeptides of Infectious Pancreatic Necrosis Virus (IPNV) comprising structural proteins VP2 and VP3 folded as an empty IPNV viral capsid that approximates the size and structural conformation of native IPNV virus.

21 Claims, 3 Drawing Sheets

OTHER PUBLICATIONS

Vakharia, V.N. 1994. Active and passive protection against variant and classic infectious bursal disease virus induced by baculovirus expressed structural proteins. Vaccine 12:452–456.

Yao, K. 1998. Generation of infectious pancreatic necrosis virus from cloned cDNA. Journal of Virology 72:8913–8920.

* cited by examiner

SUB-UNIT VACCINE FOR INFECTIOUS PANCREATIC NECROSIS VIRUS

CROSS-REFERENCE TO RELATED APPLICATIONS

This application claims priority from U.S. Provisional Patent Application No. 60/311,488 filed on Aug. 10, 2001 by Vikram N. Vakharia entitled "VACCINE FOR INFECTIOUS PANCREATIC NECROSIS VIRUS."

BACKGROUND OF INVENTION

1. Field of the Invention

The present invention relates generally to a vaccine, and more particularly, to a sub-unit vaccine comprising structural proteins VP2 and VP3 of Infectious Pancreatic Necrosis Virus (IPNV) assembled as an empty viral capsid.

2. Description of the Related Art

Epizootics of viral infections are devastating in hatcheries and ponds rearing either cold or warm water fish and repeated disease outbreaks can jeopardize the financial survival of an operation. Thus, the health of fish is critical to the survival of the aquaculture industry and effective vaccines are desperately needed.

Infectious pancreatic necrosis virus (IPNV) is the causal agent of a highly contagious and destructive disease of juvenile Rainbow and Brook trout and Atlantic salmon. Young fish (two-to four-months old) appear to be the most susceptible to IPNV infection, resulting in high mortality. In trout and salmon, IPNV usually attacks young fry about five to six weeks after their first feeding. The affected fish are darker than usual, have slightly bulging eyes and often have swollen bellies. At the beginning of an outbreak, large numbers of slow, dark fry are seen up against water outflows, and fish are seen "shivering" near the surface. The shivering results from a characteristic symptom of the disease, a violent whirling form of swimming in which the fish rotate about their long axis. If the affected fish are examined, a characteristic white mucus is seen in the stomach. The pancreas appears to be the primary target organ for the virus.

After an IPNV outbreak, the surviving fish generally become carriers of the virus. Trout that are carriers of the virus are a serious problem for the aqua-culture industry because the only control method currently available on a commercial basis for eliminating the virus in carrier fish is destruction of these fish.

Highly virulent strains of IPNV may cause greater than 90% mortality in hatchery stocks in less than four months old. Survivors of infection can remain lifelong asymptomatic carriers and serve as reservoirs of infection, shedding virus in their feces and reproductive products. The virus is capable of infecting a number of different hosts and has a worldwide presence. IPNV can have serious economic consequences for commercial trout and salmon farms and are therefore a major concern within the aquaculture industry. Therefore, IPNV is a pathogen of major economic importance to the aquaculture industry.

IPNV is the prototype of the Birnaviridae virus family. IPNV contains a bisegmented dsRNA genome, which is surrounded by a single-shelled icosahedral capsid. The larger of the two genome segments, segment A (3097 bases), encodes a 106-kDa precursor polyprotein which is processed to yield mature viral structural proteins VP2 and VP3, and VP4 (also named NS) a non-structural protein (Duncan et al. 1987). VP2 has been identified as the major host protective antigen of IPNV. The genome segment B encodes a minor internal polypeptide VP1 (94 kDa) which is the putative virion-associated RNA-dependent RNA polymerase.

An ideal vaccine for IPNV must induce protection at an early age, prevent carrier formation, and should be effective against a large number of IPNV subtypes. One approach has been the use of killed virus as a vaccine. For example, if formalin-inactivated virus is injected intraperitoneally into four week post-hatch fry, the fish becomes immunized (Dorson, J. Virol 21:242–258, 1977). However, neither immersion of the fish into a liquid suspension of killed virus nor oral administration thereof has been found effective. Thus, the main problem with using killed virus is the lack of a practical method for administration for large numbers of immature fish because injection of the vaccine is impractical.

The use of attenuated viral strains have also been used as vaccines. However, the earlier attenuated strains either failed to infect the fish or failed to induce protection. Strains with low virulence have been tested as vaccines for more virulent strains, but mortality from the vaccinating strain was either too high or protection was only moderate (Hill et al., "Studies of the Immunization of Trout Against IPN," in Fish Diseases, Third COPRAQ Session (W. Ahne, ed.), N.Y., pp. 29–36, 1980).

Recent reports have shown that expression of virus coat proteins often results in self-assembly of virus-like particles (VLP) that are essentially empty whole virions. Of these VLP-producing systems, vaccines have been proposed for poliovirus (Urakawa et al. 1989), parvovirus (Saliki et al. 1992), bluetongue virus (Belyaev et al. 1993) and infectious bursal disease virus (IBDV)—a member of the Birnaviridae family (Vakharia, et al. 1994; Bentley, et al. 1994).

However, several attempts have been made to recreate the same results for IPNV but to date these attempts have not been shown effective for various reasons. For instance, McKenna, et al. 2001 reported that virus like particles were generated through expression of Segment A by recombinant Semliki Forest Virus (SFV). Notwithstanding this alleged outcome, no conclusive proof was presented that the produced virus-like particles were indeed empty viral capsids. Several blots and electron microscopy slides show some type of virus like particles but without substantial proof of the formation of empty IPNV capsids resembling the size and 3D-structure of the native IPNV virus structure.

Magyar and Dobos, 1994 reported cloning of IPNV segment A into baculovirus expression vectors and expressing proteins pVP2, VP4 and VP3 in insect cells. However, as reported by Magyar and Dobos, using the baculovirus expression vectors in the insect cells did not show virus like particles that were correctly processed into a tertiary structure representing an empty viral capsid. Review of the process described in Magyar and Dobos it is clear that generating an empty IPNV capsid was impossible because Magyar and Dobos included the very first ORF of Segment A which encodes the minor 17-kDa nonstructural protein referred to as VP5 which partly overlaps the major ORF of VP2-VP-4-VP3 proteins. The VP5 protein is toxic to the cells and hence affects the production of any of the proteins. Thus, even though the proteins may have been expressed in the insect cells the proteins were not post-translationally modified and correctly folded into an empty IPNV capsid.

Phenix, et al. (2000) describes production of virus-like particles that were generated by expressing the IPNV VP2 protein by means of a Semliki Forest Virus expression vector. However, only the VP2 protein was expressed without expressing the VP3 protein and as such, the correct formation of an empty capsid is not formed. Further, without expression of the protein VP3, aggregates may form but without the correct conformation to form neutralizing epitope. The VP2 aggregates that were formed are smaller (25 nm) than virus-like particles that include a fully conformational folded viral capsid (approximately 50 to 65 nm and typically about 60 nm).

Inactivated IPNV vaccines have been found to be efficacious by intraperitoneal inoculation IPNV (Leong and Fryer 1993). In addition, it was shown that the complete polyprotein of segment A expressed in E. coli induced protective immunity after intraperitoneal inoculation in rainbow trout fry. However, intraperitoneal inoculation for a vaccine delivery method is not very practical and bacteria are not optimal hosts for the production of many types proteins.

Therefore, interest has centered in other eukaryotic protein expression systems, notably yeast and insect cells in culture, as possible hosts for the production of recombinant proteins. For this reason, and related reasons, there has been effort directed toward the tissue culturing of insect cells to produce recombinant proteins. Several systems have been developed for the culture of insect cells in vitro, and vectors have been developed which are capable of transgene expression in insect cells. The transforming vectors are most commonly made from a group of insect pathogenic viruses belonging to the Baculoviridae family, the viruses being known as Baculoviruses. Baculoviruses are characterized by a circular double-stranded DNA genome and a rod-shaped enveloped virion. The DNA can be manipulated to incorporate a gene which encodes a subject protein and the DNA of the baculovirus will cause the cells of its host to produce the proteins encoded in its DNA.

Another approach to the production of recombinant proteins is based on the use of live insect larvae. Such an approach uses, in effect, the insect larvae as a factory for the manufacture of the desired gene product. The transgene can be expressed in the larvae through the baculovirus expression system, allowed to proliferate, and then recovered from the larvae. Because insect larvae can be grown quickly and inexpensively and the yields obtained from insect larvae is greatly increased relative to that obtained from bacterial cells makes them an appealing alternative to cell based protein manufacturing.

Attie et al., U.S. Pat. No. 5,472,858 disclosed this approach with the tobacco hornworm. After the hornworm is infected with a recombinant baculovirus, it begins secreting the recombinant protein into its hemolymph. The hemolymph can then be withdrawn using a syringe throughout the larvae's growth. However, there is a drawback to this specific method. Although the tobacco hornworm larvae is ideal for the physical manipulation because of its large size, a great deal of manual labor is required to extract the recombinant protein if large numbers are to be cultivated.

Accordingly there is a need for an IPNV sub-unit vaccine and method of producing same that overcomes the shortcomings of the prior art, that does not exhibit the problems related to live vaccine and/or attenuated vaccines, can be easily produced and recovered, and the proteins that are expressed are post-translationally modified and correctly folded into the conformation structure that exposes neutralizing epitopes.

SUMMARY OF THE INVENTION

In one aspect the present invention relates to a sub-unit vaccine to reduce and/or prevent infection by Infectious Pancreatic Necrosis Virus (IPNV), the sub-unit vaccine comprising structural protiens VP2 and VP3 folded as an empty IPNV viral capsid. The vaccine may further comprise a reporter protien co expressed with the IPNB structural protien.

In another aspect, the present invention relates to a baculovirus expression system comprising inclusion of a cDNA clone encoding for expressed VP2-VP4-VP3 proteins that are self-assembled to form empty IPNV capsids that can be administered as a sub-unit vaccine.

In yet another aspect, the present invention relates to production of IPN virus-like particles having the structural conformation of native IPNV virus but without the RNA genome.

Still another aspect of the present invention is a method of generating IPN virus-like particles assembled as an empty IPNV viral capsid, the method comprising;
(a) providing a recombinant baculovirus comprising a polynucleotide encoding IPNV Segment A proteins VP2-VP4 -VP3, and a reporter protein;
(b) infecting insect larvae with the recombinant baculovirus; and
(c) maintaining suitable conditions for expression of IPNV Segment A proteins VP2-VP4 -VP3, and the reporter protein to generate structural proteins VP2 and VP3 assembled as an empty IPNV capsid; and
(d) recovering the empty IPNV capsid from the larvae.

DETAILED DESCRIPTION OF THE INVENTION, AND PREFERRED EMBODIMENTS THEREOF

Figure 1:
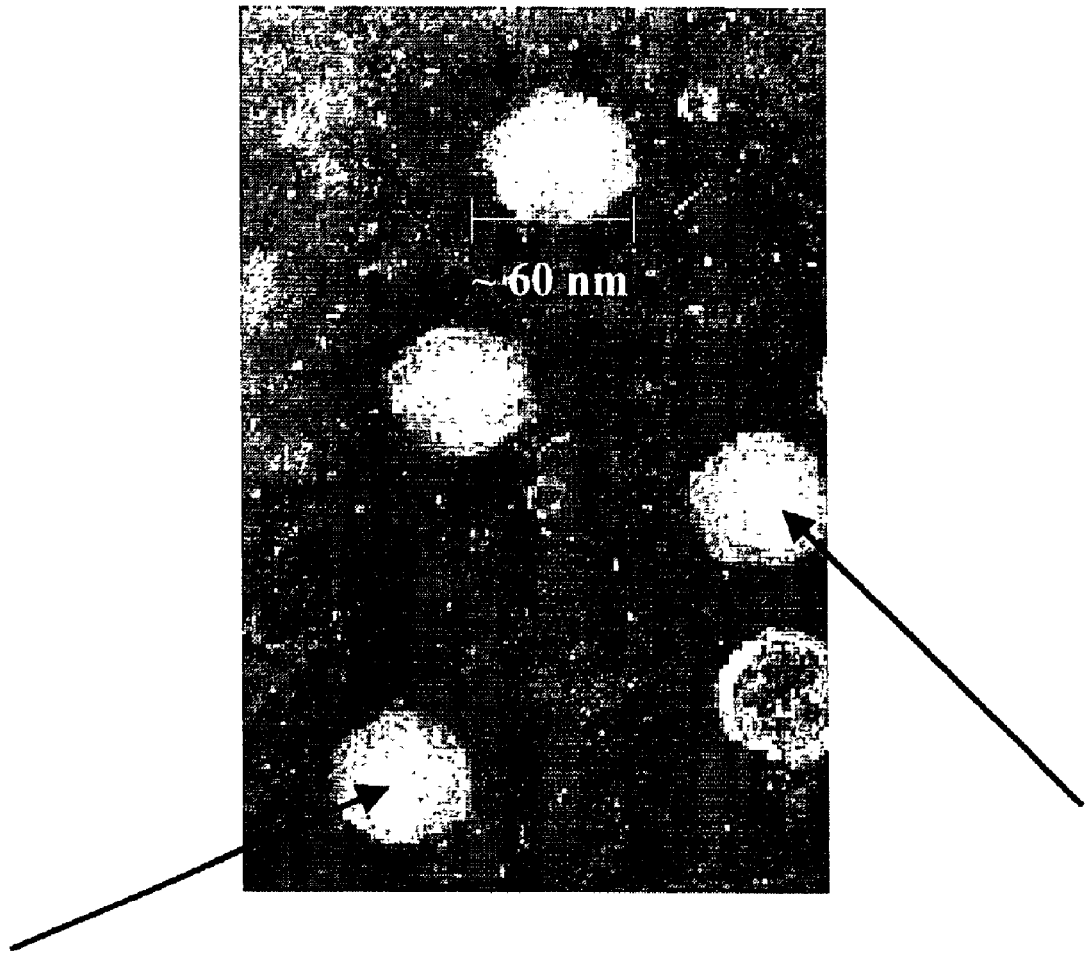
FIG. 1 is an electron microscopy slide of IPNV native full virus containing the RNA genome, the virus is sized at about 60 nm and appears white because a full virus particle, with nucleic acid, prevents stain from entering into the capsid.

The present invention is based on the discovery that expression of Infectious Pancreatic Necrosis Virus (IPNV) structural proteins VP2 and VP3, assembled as empty viral capsids that can be administered as an effective sub-unit vaccine to reduce and/or prevent infection by IPNV.

"Sub-unit vaccine" as used herein is defined as a vaccine including sub viral components that are post-translationally modified and correctly folded to act as immunogens.

"Virus-like particles" as used herein is defined as virions that lack genetic material with 3D structure and size of a native virus.

"Epitopic determinants" as used herein is defined as amino acids or amino acid sequences which correspond to epitopes recognized by one or more monoclonal antibodies.

"Reporter genes" as used herein is defined as genes that express a reporter protein, which causes some determinable characteristic in a recombinant system simultaneously with the expression of the subject gene to indicate the expression of that other gene.

Expression of the Segment A gene of IPNV that encodes for VP2-VP4-VP3 by the insertion of an baculovirus expression vector leads to the production of virus-like particles formed by the self-assembly of VP2 and VP3. A cDNA clone of segment A of the IPNV consisting of a nucleotide sequence encoding for structural proteins VP2 and VP3 and a non-structural protein VP4; and a reporter gene is constructed in tandem so that the IPNV structural proteins and reporter protein are expressed simultaneously.

Briefly, the cDNA clone containing the preferred coding and/or non-coding regions of IPNV-RNA segment A can be prepared using standard cloning procedures and methods, as described for IBDV in Mundt, E., and V. N. Vakharia. 1996, Synthetic transcripts of double-stranded birnavirus genome are infectious. *Proc. Natl. Acad. Sci. USA* 93:11131–11136, the contents of which are hereby incorporated herein by reference for all purposes. Manipulations of DNAs can be performed according to standard protocols (Sambrook, J., E. F. Fritsch, and T. Maniatis. 1989. Molecular Cloning a laboratory manual.2nd ed. Cold Spring Harbor Laboratory. Cold Spring Harbor. N.Y.).

To generate cDNA clones of a coding region of the desired structural proteins, the genomic RNA is used as a template for synthesizing and amplifying according to general RT-PCR techniques well known in the art. The desired amplified fragments are then cloned into a cloning plasmid for inclusion in the baculovirus system. Preferably a reporter gene is included to simplify the harvesting and purification of the structural proteins. With this co-expression, the actual amount of subject protein produced will be directly related to the amount of reporter protein produced.

After the foreign genetic sequences for IPNV segment A and a reporter gene have been assembled, it is then necessary to package the foreign gene into a baculovirus expression vector for expression in the insect cells. This is accomplished with a transfer vector. Any commercially available Baculovirus expression kit may be used, for instance, Invitrogen Corporation markets a kit for expression of foreign genes in insect cell systems using the Baculovirus vector under the tradename MAXBAC. The kit includes Baculovirus stock, and suitable transfer vectors which may be used with the Baculovirus to transfer foreign genes into the Baculovirus for transfection into insect cells.

Baculoviruses characteristically have a circular double-stranded DNA genome which is contained in a rod-shaped enveloped virion. The DNA can be manipulated to incorporate a gene which encodes a subject protein. Like all viruses, the DNA of the baculovirus will cause the cells of its host to produce the proteins encoded in its DNA. Consequently, if the DNA of a baculovirus is manipulated to incorporate a gene which codes for IPNV VP2-VP4-VP3 protein(s) and reporter protein and that baculovirus is allowed to infect an insect cell or insect larvae, the cells or larvae will produce the structural proteins VP2 and VP3 and the non-structural VP4.

Construction of appropriate baculovirus vectors to express a subject protein and reporter protein is apparent to one skilled in the art. The following text which is hereby incorporated herein by reference is an example of a reference that provides sufficient information and instructions to enable construction of a suitable baculovirus vector: Baculovirus Expression Vectors: A Laboratory Manual by D. R. O'Reilly, L. K. Miller and V. A. Lucklow (W. H. Freeman and Co., New York, N.Y., 1992).

Transfection of the baculovirus expression vector, including the gene encoding for the structural proteins of IPNV and reporter gene is transfected into cells, such as Sf9 cells, Sf21 and High Five cells, etc, which results in transcription of a recombinant baculovirus that can be used as an infectious agent to effect production of the recombinant subject and reporter proteins.

The recombinant baculovirus may also be used to infect insect larvae for the expression of the IPNV structural proteins and reporter proteins. Although mammalian and insect cell systems can be used to manufacture proteins, expensive and complex media are required and the bioreactors, in which the cells are grown, must be run for extended periods creating a risk of contamination of the cell culture. As such, the present invention contemplates infection of permissive insect larvae that can be infected with a baculovirus, and can be grown quickly and inexpensively. Additionally, yields can be obtained from insect larvae that cannot be obtained from cells and this fact makes insect larvae an appealing alternative to cell based protein manufacturing.

To effect infection, once a recombinant baculovirus has been constructed, a solution containing the recombinant baculovirus may be sprayed on the larvae's food for absorption therein or the baculovirus can be injected directly into the hemocoel of the larvae.

Because foreign proteins have been expressed in a variety of insect larvae; *Bombyx mori*, the silkworm (Maeda et al., 1985; Miyajima, et al., 1987), *Trichoplusia ni*, the cabbage looper larvae (Medin et al., 1990) and *Manduca sexta*, the tobacco hornworm (U.S. Pat. No. 5,471,858) there is a wide selection of insect larvae that could be utilized with this system. The larvae of the cabbage looper has been utilized and is typical of the ideal larvae envisioned for use in the present invention. Cabbage looper larvae can be ordered from commercial sources such as Entopath, Inc. (Easton, Pa.) and can be easily grown in a laboratory according to the instructions provided by the supplier. Media for the larvae can be made from alfalfa meal, pinto beans, Brewer's yeast, ascorbic acid, wheat germ, sorbic acid, vitamins, and antibiotics (aureomycin).

There is a balance to be struck as to the best stage in the larval cycle of the cabbage looper or any other suitable larvae to initiate baculovirus infection. The baculovirus kills the larvae after five days so there is a limited time in which they have to grow and express the subject protein. Because the size of the larvae is related to the amount of protein they express; small larvae produce insignificant amounts of protein, it is more effective to infect the larvae when they are larger. However, if the larvae are too large, too much baculovirus is required for infection. As such, Baculovirus infection in the fourth instar, which is the last instar prior to pupation, seems to strike the optimal balance between the larvae's size and the amount of virus required for infection.

A preferred embodiment of the present invention is a method that infects the larvae on a continuous basis and harvesting of the larvae from the production population when the reporter gene signals production of the structural proteins. A semi-continuous embodiment is also envisioned by the inventor wherein the larvae are infected at substantially the same time and then harvested individually when they express the reporter gene.

Consequently, the reporter gene of the present invention is capable of expression in insect larvae at the same time as the gene encoding the subject protein. The determinable characteristic is a change in appearance of the living larvae that can be easily visualized. Ideally, the characteristic is visible in normal light or other wavelengths of light. Thus, determination of the reporter gene's expression is simply accomplished by viewing the larvae under normal light conditions and other light conditions. Furthermore, the amount of the expressed reporter protein will directly correspond to the amount of the other protein, such as the desired structural proteins in the larvae. Consequently, the intensity of the effect created in the appearance of the living larvae by the amount of reporter protein can be used to directly measure the amount of subject protein actually present in each larvae.

An excellent choice for the role of the reporter gene is the green fluorescent protein (GFP) that was originally isolated from the jellyfish, *Aequorea victoria*, and was first described in 1962 (Shimomura et al., 1962). GFP emits bright green light when simply exposed to UV or blue light, unlike other bioluminescent reporters. The emission of green light is due to the transfer of energy from the photoprotein, aequorin, of the organism to GFP. The cDNA of GFP was cloned from *Aequorea victoria* in 1992 (Prasher et al., 1992). One such GFP is a 238 amino acid protein with a molecular weight of 28 kDa (Chalfie et al., 1994) having a major absorption peak at 395 nm and a minor peak at 470 nm with a single emission peak at 509 nm (Chalfie et. al., 1994). Preferably, the GFP gene has a nucleotide sequence selected from the group consisting of SEQ ID NOs: 1, 8, or 9.

Advantageously, fluorescence of GFP is species-independent and requires no substrate, cofactor, or additional proteins for illuminating green light. Unlike other reporter tags such as luciferase, b-galactosidase, or fluorescent-tagged antibodies, GFP does not require fixation techniques that are toxic to the cells under the investigation (Chalfie et al., 1994).

Additionally, GFP mutations have also been developed that serve well in the capacity of the reporter gene. GFPuv was optimized for UV excitation (Crameri et al., 1996). GFPuv is 18 times brighter than wild-type GFP and can be easily detected by the naked eye when excited with standard, long-wave UV light (e.g., source for many DNA transilluminator light tables). This variant contains additional amino acid mutations which increases its translational efficiency. Purified GFPuv has the same excitation and emission maxima as wild-type GFP.

Mutants of GFP are available commercially and include variants with the blue and red-shifted proteins along with several that have various intensities of green for which the codon composition has been altered . Among the commercial vendors of these mutants are Life Technologies, Inc., Clontech, Inc., and Invitrogen, Inc.

It is envisioned that the present invention will include the use of an automated system for selecting individual larvae for harvest. A monitoring capability could be added to such a system by attaching an LED/detector to each fin where the larvae hang and wiring the LED/detector and a fin to a separate controller. When the LED/detector detects a sufficient intensity of the green color of the GFP expressed in a larva, a signal would be sent to the controller which in turn would deliver voltage to the fin where the transmitting LED/detector is located. The voltage would shock the larva causing it to fall off the fin into a collection receptacle. Another possible monitoring system could resemble the conveyor belt/switching gate apparatus used by dairy egg manufacturers, where the brightest larvae are harvested. Although an automated system is preferable, since GFP mutants expressed in larvae, such as GFPuv, can be discerned by the human eye in normal laboratory light in larvae at least two or three days after infection with baculovirus and detection of GFP with human eyesight under UV light possible after at least three days, manual infection and selection for harvest is certainly feasible.

Conditions which enhance the expression of proteins VP2, VP4 and VP3 and the reporter gene, particularly green fluorescent protein, include infection with a viral loading of at least $5\times10^7$ pfu/mL recombinant baculovirus, temperature of at least about 30° C., harvesting of the larvae at least 3–5 days, more particularly at least 4 days, after post infection; at a pH of at least about 3.5 to about 4.0 and in the presence of protease inhibitors such as PMSF, EDTA and benzamidine, preferably at least about 1.5 mM.

Preservation of the larvae after selection for harvest in the present invention is envisioned to be conducted by freezing the selected larvae and then homogenizing the larvae in conditions which minimize the activity of proteases.

The previously described versions of the present invention have many advantages including the easy selection of larvae -at the point of their optimal protein expression. Because the visible expression of GFP will occur simultaneously with the expression of the IPNV structural proteins, each larvae can be selected for harvest when it is expressing the optimal amount of the subject protein. Furthermore, if the GFP is fused with at least one of the structural proteins, when expressed, it is possible in the present invention to quantify the amount of subject protein in an individual larvae. This in turn allows an estimation of the total yield from a production population to be made.

In addition, larvae which are not expressing significant amounts of the IPNV structural proteins can be removed from the production population so that resources are not expended attempting to purify the subject protein from them. Furthermore, because the larvae can be grown on inexpensive media, it is unnecessary to incur the high expense of formulating complex media and maintaining bioreactors.

The visualization of the reporter protein will permit the progress of the expression of VP2-VP4-VP3 polypeptide to be monitored through the purification process directly and indirectly. This will also serve to facilitate purification. Separation of the reporter protein from the VP2-VP4-VP3 polypeptide may be accomplished is several ways. For example, an affinity ligand could be engineered onto the reporter protein. The affinity ligand can be used to bind and separate the structural proteins from the larval extract during the initial purification.

As a further means to simply purification, the linkage between the gene for the VP2-VP4-VP3 polypeptide and the reporter gene could comprise a gene which expresses a protein that is cleaved by a specific enzyme. Once the fusion product is separated from the homogenate via the affinity ligand, it could be exposed to the enzyme which cleaves the linking protein to separate the subject protein and the reporter protein. Then, a one step purification could be performed to purify the subject protein.

Still further, in the present invention with the inclusion of the VP4 protease as part of the subject protein, it is contemplated that the VP4 may participate in the release of the GFP protein from either of the VP2 or VP3 structural proteins.

Once the VP2-VP4-VP3 polypeptide and/or VP2 and VP3 proteins are separated from the reporter protein, if it is determined that the GEP protein must be removed for effective vaccine, the purified VLPs are administered as a sub-unit vaccine to aquatic species.

It is contemplated by the inventors to include more than one strain of IPNV so that more than one type of empty viral capsid can be generated and recovered. Thus, the recovered empty viral capsids may contain epitopic determinants for more than one strain of IPNV. Since VP2 protein is the major host protective immunogen of IPNV, the present invention can include structural proteins (VP2 and VP3) from at least two different IPNV strains. Strains suitable for use in producing the present vaccine include but are not limited to West Buxton, Jasper, SP, N1, DRT, Ab, HE, TE, Canada 1, 2, 3 and VR299 strains.

Physiologically acceptable carriers for vaccination of fish are known in the art and need not be further described herein. In addition to being physiologically acceptable to the fish the carrier must not interfere with the immunological response elicited by the vaccine and/or with the expression of its polypeptide product.

Other additives, such as adjuvants and stabilizers, among others, may also be contained in the vaccine in amounts known in the art. Preferably, adjuvants such as aluminum hydroxide, aluminum phosphate, plant and animal oils, and the like, are administered with the vaccine in amounts sufficient to enhance the immune response to the IPNV. The amount of adjuvant added to the vaccine will vary depending on the nature of the adjuvant, generally ranging from about 0.1 to about 100 times the weight of the IPNV, preferably from about 1 to about 10 times the weight of the IPNV.

The vaccine of the present invention may also contain various stabilizers. Any suitable stabilizer can be used including carbohydrates such as sorbitol, mannitol, starch, sucrose, dextrin, or glucose; proteins such as albumin or casein; and buffers such as alkaline metal phosphate and the like.

The vaccine can be administered by any suitable known method of inoculating fish including but not limited to immersion, oral administration, spraying and injection. Preferably, the vaccine is administered by mass administration techniques such as immersion as conducted by a standardized immersion protocol described by McAllister and Owens (1986), the contents of which are hereby incorporated by reference herein in its entirety.

When administered by injection, the vaccines are preferably administered parenterally. Parenteral administration as used herein means administration by intravenous, subcutaneous, intramuscular, or intraperitoneal injection. Further administration may be accomplished by sonification or electroporation.

The vaccine of the present invention is administered to fish to prevent IPNV anytime before or after hatching. The term "fish" is defined to include but not be limited to fish species including trout, salmon, carp, perch, pike, eels, and char as well as mollusks and crustaceans. The vaccine may be provided in a sterile container in unit form or in other amounts. It is preferably stored frozen, below −20° C., and more preferably below −70° C. It is thawed prior to use, and may be refrozen immediately thereafter. For administration to fish, the recombinantly produced VLPs may be suspended in a carrier in an amount of about $10^2$ to $10^7$ pfu/ml, and more preferably about $10^5$ to $10^6$ pfu/ml in a carrier such as a saline solution. The sub-unit vaccine may contain the antigenic equivalent of $10^4$ to $10^7$ pfu/ml suspended in a carrier. Other carriers may also be utilized as is known in the art.

Examples of pharmaceutically acceptable carriers are diluents and inert pharmaceutical carriers known in the art. Preferably, the carrier or diluent is one compatible with the administration of the vaccine by mass administration techniques. However, the carrier or diluent may also be compatible with other administration methods such as injection, and the like.

The invention also can be used to produce combination vaccines wherein the IPNV material is combined with antigen material of other relevant fish pathogens and/or bacterial antigens. Examples of relevant fish pathogens include but are not limited to infectious hematopoietic necrosis virus (IHNV), viral hemorrhagic septicemia virus (VHSV), ISAV (Infectious salmon anemia virus), PDV (Pancreas disease virus), Irido virus and Nodavirus. Examples of relevant bacterial antigens include but are not limited to antigens from gram positive bacteria such as but not limited to *Lactococcus garvieae* and gram negative bacteria such as but not limited to *Aeromonas salmonicida*. Other relevant bacterial antigens include but are not limited to antigens from *Vibrio anguillarum, Vibrio salmonicida, Vibrio viscosus, Yersinia ruckri, Piscirickettsia salmonis, Renibacterium salmoninarum, Pasturella piscicida, Flavobacterium columnare*, and *Flavobacterium psychrophilum*.

The foregoing embodiments of the present invention are further described in the following Examples. However, the present invention is not limited by the Examples, and variations will be apparent to those skilled in the art without departing from the scope of the present invention.

Cloning and Expression of ALV122 Segment A (major ORF) and EGFP in Bac-to-Bac Baculovirus Expression System.

All DNA manipulations were carried out according to standard molecular biology techniques described by Sambrook, et at. A full length complementary DNA fragment (SEQ ID NO: 2) encoding the Segment A (VP2-VP4-VP3 of a Norwegian field isolate (Sp serotype (ALV 122)) of Infectious Pancreatic Necrosis Virus (IPNV) was generated by reverse transcription-polymerase chain reaction (RT-PCR).

To generate cDNA clones of segment A of Sp strain (ALV122) (SEQ ID NO: 2), two primer pairs (A–A5' NC plus SpA-KpnR, Spa-KpnF plus SpA-PstR) were used for RT-PCR amplification. The sequences of these primers were:

1) A-A5' NC, 5'-TAATACGACTCACTATAGGAAAGAGAGTTT CAACG-3' (SEQ ID NO: 10);
2) SpA-KpnR, 5'-GGCCATGGAGTGGTACCTTC-3' (SEQ ID NO: 11);
3) SpA-KpnF, 5'-GAAGGTACCACTCCATGGCC-3' (SEQ ID NO: 12; and
4) SpA-PstR, 5'-AAAGCTTCTGCAGGGGGCCCCCTGGGGGGC-3' (SEQ ID NO: 13).

Using genomic RNA as a template, desired overlapping cDNA fragments of segment A were synthesized and amplified according to the supplier's protocol (Perkins-Elmer). Amplified fragments were cloned into the EcoRI site of pCR2.1 vector (Invitrogen Corp.) to obtain plasmids pCR-SpA5' and SpA31. The insert DNA in all the plasmids was sequenced by the dideoxy chain termination method using an Applied Biosystem automated DNA sequencer, and the sequence data was analyzed by using PC/GENE (Intelligenetics) software. To construct a full-length cDNA clone of segment A, a representative plasmid of pCRSpA5' and pCRSpA3' clones was double-digested with restriction enzyme pairs BamHI plus KpnI and KpnI plus HindIII release 1495 and 1602 bp fragments, respectively. These fragments were then cloned between the BamHI and KpnI sites of pUC19 vector to obtain plasmid PUC19SpAALV122#7. This plasmid contained a full-length copy of segment A which encodes all for VP2-VP4-VP3.

A complementary DNA clone of energetic GFP (SEQ ID NO: 1) was amplified using primers XhoEGFPF: 5'-AACTCGAGATGGTGAGCAAGGGCGAG-3' (SEQ ID NO: 4) and XhoEGFPR: 5'-ATCTCGACTTGTACAGCTCGTCCATGC-3' (SEQ ID NO: 5). The PCR product was cloned into pCR 2.1 vector by TA cloning. (A TOPO TA cloning kit is available from InVitrogen Corp containing T vector and other components required for cloning including the pCR2.1-TOPO vector, 10× PCR buffer, salt solution, dNTP mix, control template, and control PCR primers, DH5a-T1 Competent cells (1 vial/transformation), SOC medium.) EGFP was excised using Xho I site and cloned into a pFastBac DUAL vector next to the P10 promoter to yield FastBacEGFP(p 10).

The construction of the full-length cDNA clone of segment A of IPNV strain ALV 103 of Sp serotype has been described in U.S. Patent No. 6,274,147, the contents of which are hereby incorporated herein by reference for all purposes. Using the methods described in U.S. Pat. No. 6,274,147, the major open reading frame (ORF) of segment A was amplified by PCR with the following set of primers.: SpABamF: 5'-GGGATCCATGAACACAAACAAGGC-3' (SEQ ID NO: 6) and SpAHinR: 5'-AAAGCTTACACCTCAGCGTTGTC-3' (SED ID NO: 7). The PCR product was cloned into pCR2.1 vector by TA cloning.

The SP strain ALV103 was cloned behind the polyhedrin promoter between the BamHI and HindIII sites of baculovirus vector, pBlueBac4. The recombinant plasmid BlueBac-SPA#8 was obtained This plasmid was digested with BstE II and Hind III enzymes and this fragment was replaced with a BstE II and Hind III fragment from plasmid pUC19ALV122A #7 containing the entire segment A of ALV122. The resulting plasmid carrying the major ORF of segment A from ALV122 strain was digested with BamHI and Sal I enzymes and cloned next to polyhedrin promoter of FastBacEGFP(p 10) to yield FastBacEGFP(p10)IPNA (poly). This plasmid was then used to make bacmid clone and subsequently used to generate recombinant baculovirus.

A recombinant baculovirus containing the nucleotide sequence of segment A of IPNV and the EGFP gene was obtained by the method described in the manual of O'Reilly et al. (1991) and using a BAC-TO-BAC Baculovirus Expression system available from Invitrogen. The system includes pFASTBAC™ the BAC-TO-BAC expression vector for transforming DH10Bac *E.coli* which contains a specialized Bacmid that recombines with the preferred construct via site-specific transposition to create a recombinant expression Bacmid.

The mixture was added to 0.75 ml of Grace's medium supplemented with 10% FBS in a 60-mm dish seeded with the permissive *Spodoptera frugiperda* (Sf9) cells. Following incubation at 27° C. for 4 hr, the medium was removed; the monolayer washed with Grace's medium supplemented with 10% FBS and the dish incubated at 27° C. Four to six days post transfection, the cells were observed with an inverted microscope for signs of infection. Extracellular virus was collected and plaqued on monolayer of Sf9 cells. Representative recombinant IPNV was used for infecting of insect larvae.

Infecting Insect Larvae to Generate Sufficient Guantities of Empty IPNV Capsids for Vaccination Purposes.

This example describes the optimized production of IPNV structural proteins in larvae of the cabbage looper, *Trichoplusia ni*. The eggs were obtained from a commercial supplier (Entopath, Inc., Easton, Pa.) and hatched in Styrofoam cups containing solid food (Entopath) at 30° C. The recombinant baculovirus, isolated and purified from the insect cells were used to infect the larvae by injection of 5 $\mu$l of 5×10$^6$ pfu/ml per fish. (It should be noted that infection may also be accomplished by spreading 500 $\mu$L recombinant baculovirus (5×10$^7$ pfu/ML) on the media which was obtained pre-made in Styrofoam cups (Entopath)).

The cups were covered and allowed to stand an hour for the virus to be completely absorbed by the media. The fourth instar larvae (about 4 days after hatching) were then placed into the cups (approximately about 10 to 15 larvae per cup). The cups were then inverted and the larvae were allowed to feed on the infected food at 30° C. The fecal matter dropped onto the lid so it could be discarded daily.

The infected larvae were then collected and frozen at about −60° C. until they were ready for isolation and purification of the recovered protein structures. The frozen larvae were thawed, and homogenized in phosphate buffered saline (PBS) containing 60 mM dithiothreitol (DTT), and 0.5% Triton X-100 at pH 7.0. The homogenate was then centrifuged at 4° C. to remove large debris. After centrifugation, the supernatant was also further clarified with using a 0.22 micron filter.

Figure 2:
FIG. 2 is electron microscopy slide of IPNV-type particles negatively stained with uranyl acetate showing that the virus particles are empty because the stain has entered into the structure which gives a dark appearance. The virus particles have the 3D structure of native IPN viruses but show no infectious RNA genome. The particle size corresponds to that of the native virus.

The fraction containing the expressed structural proteins was examined in an electron microscope. Empty IPNV capsids were found as shown in FIG. 2, that were similar to size and symmetry to those described for native ALV122 Sp strains as shown in FIG. 1. The particles viewed under the electron microscope were sized at about 60 nm and showing the capsid structure but having no RNA genome as compared to the fully active native IPN viruses. Thus, the shape and size of the negatively stained purified IBNV-like particles were similar to in size and shape to the native IPNV but without the infectious genomic load.

The virus particles were recognized by anti-VP2 monoclonal antibody provided in an antibody kit commercially available from Dioxotics, which further confirmed the identity with the native IPNV and suggested that the surface of the virus particles were formed by VP2 proteins. Further binding of the antibody to the virus particles were evidence of correct structural formation of the outer viral capsid which has internalized the VP3 protein. As such, the VP2 protein, carrying the major neutralizing epitope formed the external surface of the virion and the VP3 protein faces the interior of the capsid.

Efficacy of empty IPNV capsids as a sub-unit vaccine

This study was carried out at the United States Geological Survey, National Fish Health Research Laboratory, Kearneysville, W.Va. The experiment was conducted in a flow through system. The experimental design consisted of four experiments with six treatments and 3 replicates with a total of seventy-two tanks. Thirty Rainbow trout fry, with an average body weight of 0.13 g were held in one-liter polypropylene tanks and used for the study. In each experiment, fish was vaccinated at high (0.5mg/mL) and low (0.1 mg/mL) doses of the expressed IPNV structural proteins in three treatments and the other three treatments was treated with phosphate buffered saline (PBS) instead, and served as controls. In the first and second experiment, fish were subjected to high dose of the IPNV structural proteins and were challenged after two and three weeks post vaccination respectively, with Sp and VR-299 strains of IPNV. Low dose of expressed structural IPNV protein was used in the third and fourth experiment with similar post vaccination exposure times. Overall, the experimental set up consisted of 72 tanks (6 groups×3 replicates×2 vaccine doses×2 time intervals=72). The treatment groups and the number of tanks that were used for the study are shown in Table 1.

TABLE 1

Treatment groups and the total number of tanks used for the study. Control groups were treated with phosphate buffered saline (PBS) instead of expressed IPNV structural proteins.

| Treatment | Replicates | Vaccine Dose | Exposure time | Total Tanks |
|---|---|---|---|---|
| Control Groups | | | | |
| No vaccine + No Challenge | 3 | 2 (PBS) | 2 | 12 |
| No Vaccine + ALV 122 (Sp) | 3 | 2 (PBS) | 2 | 12 |
| No Vaccine + VR-299 | 3 | 2 (PBS) | 2 | 12 |
| Immunized + Groups | | | | |
| Immunized + No challenge | 3 | 2 | 2 | 12 |
| Immunized + ALV122 | 3 | 2 | 2 | 12 |
| Immunized + VR-299 | 3 | 2 | 2 | 12 |

For vaccination and challenging of the fish, a standardized immersion challenge described by McAllister and Owens (1986) for IPNV was followed. For vaccination, the purified larval homogenate containing expressed IPNV proteins was used. For virus challenge, stock virus was diluted in PBS and added to tanks containing fish at a density of 1 g of fish per 25 mL of water to achieve a concentration of $10^5$ PFU/mL. During both vaccination and challenge, fish were exposed for 5 hours with static condition and aeration. Water flow was resumed at a rate of 250 mL/min after the end of exposure.

Mortality was monitored over a period of 28 days in all the four experiments. The dead fish were collected daily and frozen at $-20°$ C. until the analysis. At the end of all the experiments, seventy-five fish from both control and vaccinated groups (twenty-five from each replicate) including the survivors and the dead fish were individually analyzed for the presence of IPNV by viral plaque assay. Histopathological studies also will be performed to examine whether the vaccine can prevent lesions in the internal organs.

Results

Figure 3:
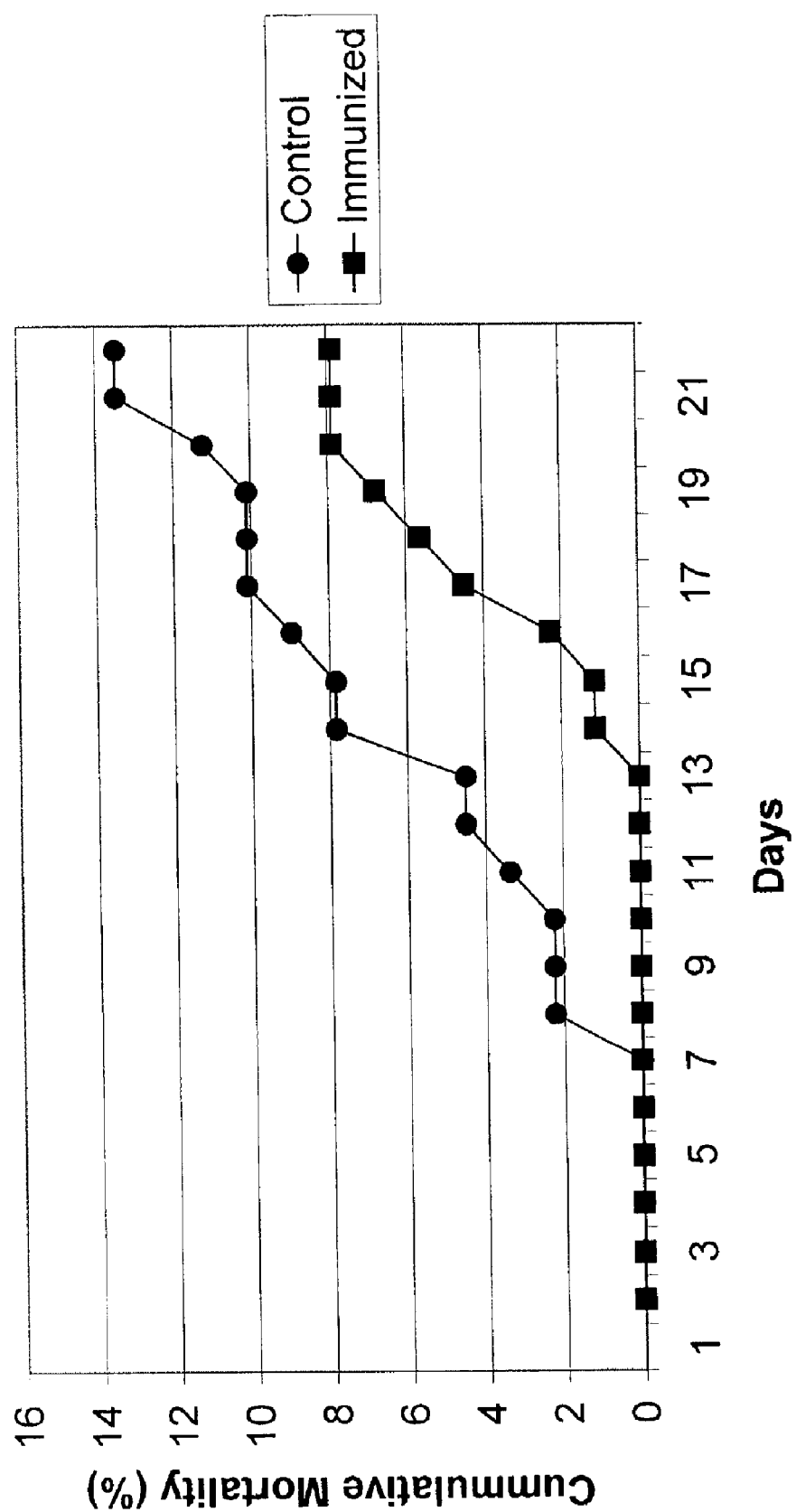
FIG. 3 is a graphical representation of cumulative mortality rates of rainbow trout that were challenged with VR299

In experiment 1, fish were immunized with high dose of IPNV expressed structural proteins and challenged two weeks post-vaccination with Sp and VR299 strains of IPNV. Mortality due to primary infection started to appear on the seventh day in the control group that was not immunized but challenged with VR299. Mortality in the immunized group on the other hand, started appearing on the thirteenth day in the VR299 challenged group, which indicates that the vaccine was able to prevent the primary infection. It was found that the cumulative mortality rate in the control group was 13.5% while in the immunized group it was only 8% (FIG. 3). The result indicated that the expressed proteins of Sp strain that was isolated in Norway can confer a partial cross protection against VR299 strain that was isolated from a field outbreak in USA. Neither the control nor the treated group showed mortality when exposed to the Sp strain of IPNV. The Sp isolate that was used in the study was originally isolated from a field outbreak in Norway from Atlantic salmon. The results obtained indicate that the rainbow trout used in the study might not have the receptors for the virus entry and hence may not be susceptible to Sp strain.

The lower doses used in Experiments 3 and 4 showed no difference in the mortality rate indicating that the effectiveness of the vaccine is dose dependent.

REFERENCES

All cited references are hereby incorporated herein by reference for all purposes.

Belyaev, A. S. and P. Roy. 1993 Development of baculovirus triple and quadruple expression vectors: co-expression of three or four bluetongue virus proteins and the synthesis of bluetongue virus-like particles in insect cells. Nucl. Acids. Res. 21(5):1219–1223.

Bentley, W E., M. Y. Wang and V. N. Vakharia. 1994. Development of an efficient bioprocess for poultry vaccines using high-density insect cell culture. Ann. New York Acad. Sci. 745: 336–359.

Cha, H J., N. G. Dalal, M. Q. Pham, V. N. Vakharia, G. Rao, W E. Bentley. 1999. Insect larval expression process is optimized by generating fusions with green fluorescent protein. Biotechnol. Bioeng. 65:316–324.

Duncan, R., E. Nagy, P. J. Krell and P. Dobos. 1987. Synthesis of the infectious pancreatic necrosis virus polyprotein, detection of a virus-encoded protease, and line structure mapping of genome segment A coding regions. 3. Virol. 61:3655–3664.

Leong, J. C. and J. L. Fryer. 1993. Viral vaccines for aquaculture. Pages 225–240 in M. Faisal and F. M. Hetrick, eds. Annual Review of Fish Diseases. Vol.3. Pergamon Press, New York.

Maeda, S. 1989. Expression of foreign genes in insects using baculovirus vectors. Ann. Rev. Entomol. 34:351–72.

Magyar, G., and Dobos, P. (1994). Expression of infectious pancreatic necrosis virus polyprotein and VP1 in insect cells and the detection of the polyprotein in purified virus. Virology 198: 437–445.

McAllister P. E., Owens, W. J., Infectious Pancreatic Necrosis Virus—Protocol for a Standard Challenge to Brook Trout, Transactions of the American Fisheries Society, 115 (3): 466–470 May 1986.

McKenna, B. M., Fitzpatrick, R. M., Phenix, K. V., Todd, D., Vaughan, L. M., and Atkins, G. J., 2001. Formation of Infectious Pancreatic Necrosis Virus-like Particles Following Expression of Segment A by Recombinant Semliki Forest Virus, Mar. Biotechnol. 3, 103–110.

O'Reilly, D. K., L. K. Miller and V A Luckow. 1991. Baculovirus expression vectors: A laboratory manual. $1^{st}$ edition. W. H. Freeman and Co., New York.

Phenix, K. V., McKenna, B., Fitzpatrick, R., Vaughan, L., Atkins, G., Liljestrom, P and Todd, D., 2000. Cell Culture Evaluation of the Semliki Forest Virus Expression System As a Novel Approach for Antigen Delivery and Expression in Fish, Mar. Biotechnol. 2, 27–37.

Saliki, J. T., B. Mizak and H. P. Flore. 1992. Canine parvovirus empty capsids produced by expression in a baculovirus vector: use in analysis of viral properties and immunization. J. Gen. Virol. 73:369.

Sambrook, J., E. F. Fritsch and T. Maniatis. 1989. Molecular cloning: a laboratory manual, 2$^{nd}$ ed Cold Spring Harbor Laboratory, Cold Spring Harbor, N.Y.

Urakawa, T., M. Ferguson, P. D. Minor, J. Cooper, M. Sullivan, J. W. Almond and D. H. L. Bishop. 1989. Synthesis of immunogenic, but non-infectious, poliovirus particles in insect cells by a baculovirus expression vector. J. Gen. Virol. 70:1453–1463.

Vakharia, V. N., D. B. Snyder, D. Lutticken, S. A. Mengel-Whereat, P. K. Savage, G. H. Edwards and M A Goodwin. 1994. Active and passive protection against variant and classic infectious bursal disease virus induced by baculovirus expressed structural proteins. Vaccine 12:452–456.

Yao, K. and V. N. Vakharia 1998. Generation of infectious pancreatic necrosis virus from cloned cDNA J. Virol. 72:8913–8920.

What is claimed is:

1. A sub-unit vaccine for controlling Infectious Pancreatic Necropis Virus (IPNV) in aquatic species, the sub-unit vaccine comprising IPNV structural proteins comprising VP2 and VP3 of a single native virus assembled as an empty IPNV capsid, wherein the empty IPNV capsid approximates the size and conformation of the native IPN virus, and wherein the VP2 and VP3 structural proteins are encoded by amino acid sequence SEQ ID NO: 3.

2. The vaccine according to claim 1, further comprising a green fluorescent protein.

3. The vaccine according to claim 1, further comprising an antigen from an aquatic virus other than IPNV selected from the group consisting of: infectious hematopoictic necrosis virus (IHNV), viral hemorrhagic septicemia virus (VHSV), ISAV (Infectious salmon anemia virus), PDV (Pancreas disease virus), Irido virus, and Nodavirus.

4. The vaccine according to claim 1, wherein the empty viral capsid has a diameter of about 50 to about 65 nm.

5. The vaccine according to claim 1, further comprising a physiologically acceptable carrier for fish.

6. A sub-unit vaccine for controlling Infectious Pancreatic Necrosis Virus (IPNV) in aquatic species, the sub-unit vaccine comprising IPNV structural proteins VP2 and VP3 assembled as an empty IPNV capsid, wherein the VP2 and VP3 structural proteins are encoded by nucleotide sequence SEQ 11) NO: 2.

7. A sub-unit vaccine for controlling Infectious Pancreatic Necrosis Virus (IPNV) in aquatic species, the sub-unit vaccine comprising IPNV structural proteins consisting of VP2 and VP3 of a single native virus assembled as an empty IPNV capsid, wherein the empty IPNV capsid approximates the size and conformation of the native IPN virus, wherein the VP2 and VP3 structural proteins are encoded by amino acid sequence SEQ ID NO: 3 and wherein the wherein the empty viral capsid has a diameter of about 50 to about 65 nm.

8. A method for reducing and/or preventing infection of IPNV in marine fish by administrating an effective amount of a sub-unit vaccine comprising IPNV structural proteins consisting of VP2 and VP3 from a single native strain assembled as an empty IPNV capsid that approximates the size and conformation of the native IPN virus, and wherein the VP2 and VP3 structural proteins are encoded by amino acid sequence SEQ ID NO: 3.

9. The method according to claim 8, wherein the vaccine further comprises an antigen from an aquatic virus other than IPNV selected from the group consisting of: infectious hematopoietic necrosis virus (IHNV), viral hemorrhagic septicemia virus (VHSV), ISAV (Infectious salmon anemia virus), PDV (Pancreas disease virus), Irido virus, and Nodavirus.

10. The method according to claim 8, wherein the empty viral capsid resembles the 3D structure of native IPNV particles and does not include an infectious RNA genome.

11. The method according to claim 8, wherein the empty IPNV capsid has a diameter of about 50 to about 65 nm.

12. A baculovirus expression vector comprising a polynucleotide sequence encoding for structural proteins VP2-VP4-VP3 (SEQ ID NO. 3, of infectious' pancreatic necrosis virus and a green fluorescent protein, wherein the polynucleotide sequence encoding the structural proteins is SEQ ID NO: 2.

13. The baculovirus expression vector according to claim 12, wherein the polynucleotide sequence encoding the green fluorescent protein is SEQ ID NO: 1.

14. A host cell transfected with the baculovirus expression vector according to claim 13.

15. The baculovirus expression vector according to claim 12, wherein the polynucleotide sequence encoding for the green fluorescent protein is selected from the group consisting of SEQ ID NO: 8, and SEQ ID NO: 9.

16. A host cell transfected with the expression vector according to claim 15.

17. A host cell transfected with the baculovirus expression vector according to claim 12.

18. The host cell according to claim 12, wherein the host cell is an insect cell.

19. A method of generating structural proteins of IPNV assembled as an empty viral capsid comprising the steps of:
  (a) providing a recombinant baculovirus comprising a polynucleotide encoding IPNV Segment A proteins consisting of VP2,-VP4-VP3 from a single native virus, and a reporter protein, wherein the polynucleotide encoding IPNV segment A proteins is SEQ ID NO: 2;
  (b) infecting insect larvae with the recombinant baculovirus; and
  (c) maintaining suitable conditions for expression of IPNV Segment A proteins VP2,-VP4-VP3, to generate structural proteins VP2 and VP3 assembled as an empty IPNV capsid; and
  (d) recovering the empty IPNV capsid from the larvae, wherein the empty IPNV capsid approximates the size and conformation of the native IPNV virus and is encoded by amino acid sequence SEQ ID NO: 3.

20. The method according to claim 17, wherein the larvae are harvested when the reporter protein is expressed.

21. The method according to claim 16, wherein the suitable conditions comprise:
  infecting the larvae wish a viral loading of at least $5 \times 10^7$ pfu/mL recombinant baculovirus;
  maintaining a temperature of at least about 30° C; and
  harvesting of the larvae at least 3–5 days after post infection at a pH of at least about 3.5 to about 4.0.

* * * * *

UNITED STATES PATENT AND TRADEMARK OFFICE
CERTIFICATE OF CORRECTION

PATENT NO. : 6,936,256 B2
DATED : August 30, 2005
INVENTOR(S) : Vikram N. Vakharia It is certified that error appears in the above-identified patent and that said Letters Patent is hereby corrected as shown below:

Title page,
Item [56], References Cited, OTHER PUBLICATIONS,
"Magyar, G. 1994. Expression of infectious pancreatic necrosis virus polyprotein and VPI in insect cells and the detection of the polyprotein in purified virus. Virology 198:437-445." should be
-- Magyar, G. 1994. Expression of infectious pancreatic necrosis virus polyprotein and VP1 in insect cells and the detection of the polyprotein in purified virus. Virology 198:437-445. --.

Column 4,
Line 4, "the IPNB structural" should be -- the IPNV structural --.
Lines 8, 19-20 and 24, "VP2-VP4-VP3" should be -- VP2, --VP4-VP3 --.
Lines 27-28, "(d) recovering the empty IPNV capsid from the larvae. BRIEF DESCRIPTION OF THE DRAWINGS" should be -- (d) recovering the empty IPNV capsid from the larvae. Another aspect relates to a sub-unit vaccine for controlling Infectious Pancreatic Necrosis Virus (IPNV) in aquatic species, the sub-unit vaccine comprising IPNV structural proteins VP2 and VP3 assembled as an empty IPNV capsid that corresponds to the 3D-structure of a native IPN virus and does not include an infectious RNA genome. Other aspects and features of the invention will be more fully apparent from the ensuing disclosure and the appended claims. BRIEF DESCRIPTION OF THE DRAWINGS --.

Column 8,
Line 63, "GEP protein" should be -- GFP protein --.

Column 10,
Line 33, "(ALV 122)" should be -- (ALV122) --.

Column 11,
Line 18, "(ALV 103)" should be -- (ALV103) --.
Line 63, "Guantities" should read -- Quantities --.

Column 31,
Line 56, "hematopoictic" should be -- hematopoietic --.

UNITED STATES PATENT AND TRADEMARK OFFICE
CERTIFICATE OF CORRECTION

PATENT NO.    : 6,936,256 B2
DATED         : August 30, 2005
INVENTOR(S)   : Vikram N. Vakharia It is certified that error appears in the above-identified patent and that said Letters Patent is hereby corrected as shown below:

Column 32,
Line 45, "SEQ 11) NO: 2." should be -- SEQ IDNO: 2. --.

Column 33,
Line 11, "(SEQ ID NO.3 of infectious' pancreatic" should be -- (SEQ ID NO.3) of infectious' pancreatic --.
Line 28, "The host cell according to claim 12" should be -- The host cell according to claim 17 --.

Column 34,
Line 23, "larvae wish" should be -- larvae with --.
Lines 26-27, "after post infection" should be -- after infection --.

Signed and Sealed this

Twenty-eighth Day of February, 2006

JON W. DUDAS
*Director of the United States Patent and Trademark Office*

SEQUENCE LISTING

<160> NUMBER OF SEQ ID NOS: 13

<210> SEQ ID NO 1
<211> LENGTH: 720
<212> TYPE: DNA
<213> ORGANISM: Aequorea victoria

<400> SEQUENCE: 1

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctacccga ccacatgaag      240 cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gacccccaacg agaagcgcga tcacatggtc    660
ctgctggagt tcgtgaccgc cgccgggatc actctcggca tggacgagct gtacaagtaa     720
```

<210> SEQ ID NO 2
<211> LENGTH: 3097
<212> TYPE: DNA
<213> ORGANISM: Infectious pancreatic necrosis virus

<400> SEQUENCE: 2

```
ggaaagagag tttcaacgtt agtggtaacc cacgagcgga gagctcttac ggaggagctc      60
tccgtcgatg gcgaaagccc tttctaacaa acaaacaaac aatctatatc aatgcaagat     120
gaacacaaac aaggcaaccg caacttacct gaaatccatt atgcttccag agactggacc     180
agcaagcatc ccggacgaca taacggagag acacatctta aaacaagaga cctcgtcata     240
caacttagag gtctccgaat caggaagtgg cattcttgtt tgtttccctg gggcaccagg     300
ctcacggatc ggtgcacact acagatggaa tgcgaaccaa acggggctgg agttcgacca     360
gtggctggag acgtcgcagg acctgaagaa agccttcaac tacgggaggc tgatctcaag     420
gaaatatgac atccaaagct ccacactacc ggccggtctc tatgctctga acgggacgct     480
caacgctgcc accttcgaag gcagtctgtc tgaggtggag agcctgacct acaacagcct     540
```

```
gatgtcccta acaacgaacc cccaggacaa agtcaacaac cagctggtga ccaaaggagt    600
cacagtcctg aatctaccaa cagggttcga caaaccatac gtccgcctag aggacgagac    660
accccagggt ctccagtcaa tgaacggggc caagatgagg tgcacagctg caactgcacc    720
gcggaggtac gagatcgacc tcccatccca acgcctaccc ccgttactg cgacaggaac     780 cctcaccact ctctacgagg gaaacgccga catcgtcaac tccacgacag tgacgggaga    840
cataaacttc agtctgacag aacaacccgc agtcgagacc aagttcgact tccagctgga    900
cttcatgggc cttgcaacg acgtcccagt tgtcacagtg gtcagctccg tgctggccac     960
aaatgacaac tacagaggag tctcagccaa gatgacccag tccatcccga ccgagaacat   1020
cacaaagccg atcaccaggg tcaagctgtc atacaagatc aaccagcaga cagcaatcgg   1080
caacgtcgcc accctgggca caatgggtcc agcatccgtc tccttctcat cagggaacgg   1140
aaatgtcccc ggcgtgctca gaccaatcac actggtggcc tatgagaaga tgacaccgct   1200
gtccatcctg accgtagctg gagtgtccaa ctacgagctg atcccaaacc cagaactcct   1260
aaagaacatg gtgacacgct atggcaagta cgaccccgaa ggtctcaact atgccaagat   1320
gatcctgtcc cacagggaag agctggacat caggacagtg tggaggacag aggagtacaa   1380
ggagaggacc agagtcttca cgaaatcac ggacttctcc agtgacctgc ccacgtcaaa    1440
ggcatggggc tggagagaca tagtcagagg aattcggaaa gtcgcagctc ctgtactgtc   1500
cacgctgttt ccaatggcag caccactcat aggaatggca gaccaattca ttggagatct   1560
caccaagacc aacgcagcag gcggaaggta ccactccatg gccgcaggag ggcgctacaa   1620
agacgtgctc gagtcctggg caagcggagg gcccgacgga aaattctccc gagccctcaa   1680
gaacaggctg gagtccgcca actacgagga agtcgagctt ccacccccct caaaaggagt   1740
catcgtccct gtggtgcaca cagtcaagag cgcaccaggc gaggcattcg ggtccctggc   1800
aatcataatt ccaggggagt accccgagct tctagatgcc aaccagcagg tcctatccca   1860
cttcgcaaac gacaccggga gcgtgtgggg cataggagag acatacccct cgagggaga    1920 caacatgtgc tacactgcac tcccactcaa ggagatcaaa agaaacggga acatagtagt   1980
cgagaagatc tttgctggac caatcatggg tccctctgct caactaggac tgtccctact   2040
agtgaacgac atcgaggacg gagttccaag gatggtattc accggcgaaa tcgccgatga   2100
cgaggagaca atcataccaa tctgcggtgt agacatcaaa gccatcgcag cccatgaaca   2160
agggctgcca ctcatcggca accaaccagg agtggacgag gaggtgcgaa acacatccct   2220
ggccgcacac ctgatccaga ccggaaccct gcccgtacaa cgcgcaaagg gctccaacaa   2280
gaggatcaag tacctgggag agctgatggc atcaaatgca tccgggatgg acgaggaact   2340
gcaacgcctc ctgaacgcca caatggcacg ggccaaagaa gtccaggacg ccgagatcta   2400
caaacttctt aagctcatgg catggaccag aaagaacgac ctcaccgacc acatgtacga   2460
gtggtcaaaa gaggaccccg atgcactaaa gttcggaaag ctcatcagca cgccaccaaa   2520
gcaccccgag aagcccaaag gaccagacca acaccatgcc caagaggcga gagccacccg   2580
catatcactg gacgccgtga gagccggggc ggacttcgcc acaccggaat gggtcgcgct   2640
gaacaactac cgcggcccat ctcccgggca gttcaagtac tacctgatca ctggacgaga   2700
accagaacca ggcgacgagt acgaggacta cataaaacaa cccattgtga aaccgaccga   2760
catgaacaaa atcagacgtc tagccaacag tgtgtacggc ctcccacacc aggaaccagc   2820
accagaggag ttctacgatg cagttgcagc tgtattcgca cagaacgag gcagaggtcc    2880 cgaccaggac caaatgcaag acctcaggga gctcgcaaga cagatgaaac gacgaccccg   2940
```

```
gaacgccgat gcaccacgga gaaccagagc gccagcggaa ccggcaccgc ccggacgctc    3000
aaggttcacc cccagcggag acaacgctga ggtgtaacga ctactctctt tcctgactga    3060
tcccctggcc aaaaccccgg ccccccaggg ggccccc                             3097
```

<210> SEQ ID NO 3
<211> LENGTH: 972
<212> TYPE: PRT
<213> ORGANISM: Infectious pancreatic necrosis virus

<400> SEQUENCE: 3

```
Met Asn Thr Asn Lys Ala Thr Ala Thr Tyr Leu Lys Ser Ile Met Leu
1               5                   10                  15

Pro Glu Thr Gly Pro Ala Ser Ile Pro Asp Asp Ile Thr Glu Arg His
            20                  25                  30

Ile Leu Lys Gln Glu Thr Ser Ser Tyr Asn Leu Glu Val Ser Glu Ser
        35                  40                  45

Gly Ser Gly Ile Leu Val Cys Phe Pro Gly Ala Pro Gly Ser Arg Ile
    50                  55                  60

Gly Ala His Tyr Arg Trp Asn Ala Asn Gln Thr Gly Leu Glu Phe Asp
65                  70                  75                  80

Gln Trp Leu Glu Thr Ser Gln Asp Leu Lys Lys Ala Phe Asn Tyr Gly
                85                  90                  95

Arg Leu Ile Ser Arg Lys Tyr Asp Ile Gln Ser Ser Thr Leu Pro Ala
            100                 105                 110

Gly Leu Tyr Ala Leu Asn Gly Thr Leu Asn Ala Ala Thr Phe Glu Gly
        115                 120                 125

Ser Leu Ser Glu Val Glu Ser Leu Thr Tyr Asn Ser Leu Met Ser Leu
    130                 135                 140

Thr Thr Asn Pro Gln Asp Lys Val Asn Asn Gln Leu Val Thr Lys Gly
145                 150                 155                 160

Val Thr Val Leu Asn Leu Pro Thr Gly Phe Asp Lys Pro Tyr Val Arg
                165                 170                 175

Leu Glu Asp Glu Thr Pro Gln Gly Leu Gln Ser Met Asn Gly Ala Lys
            180                 185                 190

Met Arg Cys Thr Ala Ala Thr Ala Pro Arg Arg Tyr Glu Ile Asp Leu
        195                 200                 205

Pro Ser Gln Arg Leu Pro Pro Val Thr Ala Thr Gly Thr Leu Thr Thr
    210                 215                 220

Leu Tyr Glu Gly Asn Ala Asp Ile Val Asn Ser Thr Thr Val Thr Gly
225                 230                 235                 240

Asp Ile Asn Phe Ser Leu Thr Glu Gln Pro Ala Val Glu Thr Lys Phe
                245                 250                 255

Asp Phe Gln Leu Asp Phe Met Gly Leu Asp Asn Asp Val Pro Val Val
            260                 265                 270

Thr Val Val Ser Ser Val Leu Ala Thr Asn Asp Asn Tyr Arg Gly Val
        275                 280                 285

Ser Ala Lys Met Thr Gln Ser Ile Pro Thr Glu Asn Ile Thr Lys Pro
    290                 295                 300

Ile Thr Arg Val Lys Leu Ser Tyr Lys Ile Asn Gln Gln Thr Ala Ile
305                 310                 315                 320

Gly Asn Val Ala Thr Leu Gly Thr Met Gly Pro Ala Ser Val Ser Phe
                325                 330                 335

Ser Ser Gly Asn Gly Asn Val Pro Gly Val Leu Arg Pro Ile Thr Leu
```

-continued

```
                340                 345                 350
Val Ala Tyr Glu Lys Met Thr Pro Leu Ser Ile Leu Thr Val Ala Gly
            355                 360                 365

Val Ser Asn Tyr Glu Leu Ile Pro Asn Pro Glu Leu Leu Lys Asn Met
370                 375                 380

Val Thr Arg Tyr Gly Lys Tyr Asp Pro Glu Gly Leu Asn Tyr Ala Lys
385                 390                 395                 400

Met Ile Leu Ser His Arg Glu Leu Asp Ile Arg Thr Val Trp Arg
                405                 410                 415

Thr Glu Glu Tyr Lys Glu Arg Thr Arg Val Phe Asn Glu Ile Thr Asp
            420                 425                 430

Phe Ser Ser Asp Leu Pro Thr Ser Lys Ala Trp Gly Trp Arg Asp Ile
            435                 440                 445

Val Arg Gly Ile Arg Lys Val Ala Ala Pro Val Leu Ser Thr Leu Phe
450                 455                 460

Pro Met Ala Ala Pro Leu Ile Gly Met Ala Asp Gln Phe Ile Gly Asp
465                 470                 475                 480

Leu Thr Lys Thr Asn Ala Ala Gly Gly Arg Tyr His Ser Met Ala Ala
                485                 490                 495

Gly Gly Arg Tyr Lys Asp Val Leu Glu Ser Trp Ala Ser Gly Gly Pro
            500                 505                 510

Asp Gly Lys Phe Ser Arg Ala Leu Lys Asn Arg Leu Glu Ser Ala Asn
            515                 520                 525

Tyr Glu Glu Val Glu Leu Pro Pro Ser Lys Gly Val Ile Val Pro
            530                 535                 540

Val Val His Thr Val Lys Ser Ala Pro Gly Glu Ala Phe Gly Ser Leu
545                 550                 555                 560

Ala Ile Ile Ile Pro Gly Glu Tyr Pro Glu Leu Leu Asp Ala Asn Gln
                565                 570                 575

Gln Val Leu Ser His Phe Ala Asn Asp Thr Gly Ser Val Trp Gly Ile
            580                 585                 590

Gly Glu Asp Ile Pro Phe Glu Gly Asp Asn Met Cys Tyr Thr Ala Leu
            595                 600                 605

Pro Leu Lys Glu Ile Lys Arg Asn Gly Asn Ile Val Val Glu Lys Ile
            610                 615                 620

Phe Ala Gly Pro Ile Met Gly Pro Ser Ala Gln Leu Gly Leu Ser Leu
625                 630                 635                 640

Leu Val Asn Asp Ile Glu Asp Gly Val Pro Arg Met Val Phe Thr Gly
                645                 650                 655

Glu Ile Ala Asp Asp Glu Glu Thr Ile Ile Pro Ile Cys Gly Val Asp
            660                 665                 670

Ile Lys Ala Ile Ala Ala His Glu Gln Gly Leu Pro Leu Ile Gly Asn
            675                 680                 685

Gln Pro Gly Val Asp Glu Glu Val Arg Asn Thr Ser Leu Ala Ala His
            690                 695                 700

Leu Ile Gln Thr Gly Thr Leu Pro Val Gln Arg Ala Lys Gly Ser Asn
705                 710                 715                 720

Lys Arg Ile Lys Tyr Leu Gly Glu Leu Met Ala Ser Asn Ala Ser Gly
                725                 730                 735

Met Asp Glu Glu Leu Gln Arg Leu Leu Asn Ala Thr Met Ala Arg Ala
            740                 745                 750

Lys Glu Val Gln Asp Ala Glu Ile Tyr Lys Leu Leu Lys Leu Met Ala
            755                 760                 765
```

```
Trp Thr Arg Lys Asn Asp Leu Thr Asp His Met Tyr Glu Trp Ser Lys
    770                 775                 780
Glu Asp Pro Asp Ala Leu Lys Phe Gly Lys Leu Ile Ser Thr Pro Pro
785                 790                 795                 800
Lys His Pro Glu Lys Pro Lys Gly Pro Asp Gln His His Ala Gln Glu
                805                 810                 815
Ala Arg Ala Thr Arg Ile Ser Leu Asp Ala Val Arg Ala Gly Ala Asp
            820                 825                 830
Phe Ala Thr Pro Glu Trp Val Ala Leu Asn Asn Tyr Arg Gly Pro Ser
            835                 840                 845
Pro Gly Gln Phe Lys Tyr Tyr Leu Ile Thr Gly Arg Glu Pro Glu Pro
850                 855                 860
Gly Asp Glu Tyr Glu Asp Tyr Ile Lys Gln Pro Ile Val Lys Pro Thr
865                 870                 875                 880
Asp Met Asn Lys Ile Arg Arg Leu Ala Asn Ser Val Tyr Gly Leu Pro
                885                 890                 895
His Gln Glu Pro Ala Pro Glu Glu Phe Tyr Asp Ala Val Ala Ala Val
            900                 905                 910
Phe Ala Gln Asn Gly Gly Arg Gly Pro Asp Gln Asp Gln Met Gln Asp
            915                 920                 925
Leu Arg Glu Leu Ala Arg Gln Met Lys Arg Arg Pro Arg Asn Ala Asp
930                 935                 940
Ala Pro Arg Arg Thr Arg Ala Pro Ala Glu Pro Ala Pro Pro Gly Arg
945                 950                 955                 960
Ser Arg Phe Thr Pro Ser Gly Asp Asn Ala Glu Val
                965                 970

<210> SEQ ID NO 4
<211> LENGTH: 26
<212> TYPE: DNA
<213> ORGANISM: Artificial sequence
<220> FEATURE:
<223> OTHER INFORMATION: Synthetic construct

<400> SEQUENCE: 4
aactcgagat ggtgagcaag ggcgag                                    26

<210> SEQ ID NO 5
<211> LENGTH: 27
<212> TYPE: DNA
<213> ORGANISM: Artificial Sequence
<220> FEATURE:
<223> OTHER INFORMATION: Synthetic Construct

<400> SEQUENCE: 5
atctcgactt gtacagctcg tccatgc                                   27

<210> SEQ ID NO 6
<211> LENGTH: 24
<212> TYPE: DNA
<213> ORGANISM: Artificial Sequence
<220> FEATURE:
<223> OTHER INFORMATION: Synthetic Construct

<400> SEQUENCE: 6
gggatccatg aacacaaaca aggc                                      24

<210> SEQ ID NO 7
<211> LENGTH: 23
```

<210> SEQ ID NO 8
<211> LENGTH: 5170
<212> TYPE: DNA
<213> ORGANISM: Artificial Sequence
<220> FEATURE:
<223> OTHER INFORMATION: Synthetic Construct

<400> SEQUENCE: 7
aaagcttaca cctcagcgtt gtc    23

<210> SEQ ID NO 8
<211> LENGTH: 5170
<212> TYPE: DNA
<213> ORGANISM: Aequorea victoria
<220> FEATURE:
<221> NAME/KEY: misc_feature
<222> LOCATION: (651)..(651)
<223> OTHER INFORMATION: n can be a, g, t or c

<400> SEQUENCE: 8

| | | | | | |
|---|---|---|---|---|---|
| aagcttcaaa | ttaagtcagc | tccttaaatg | aaagataata | aagtgtagtt | caagaactat | 60 |
| atgaatgatg | tgttttcaga | taaccaaaat | ggggaaaaac | atgctaaagt | cagcatattt | 120 |
| ttggaaaatt | gatgacgtca | tcatgacgtc | gttttgatga | caaaacttat | tataagcgaa | 180 |
| ttcttatatt | tttacaggat | aacaaagatg | agtaaaggag | aagaactttt | cactggagtt | 240 |
| gtcccaattc | ttgttgaatt | agatggtgat | gttaatgggc | acaaattctc | tgtcagtgga | 300 |
| gagggtgaag | gtgatgcaac | atacggaaaa | cttacccctta | aatttatttg | cactactgga | 360 |
| aagctacctg | ttccatggcc | aacacttgtc | actactttct | cttatggtgt | tcagtaagtg | 420 |
| catttttatac | tcttttaata | tcagtgttaa | gaaaatcaag | tgtcttgcta | tttttttcgat | 480 |
| tattggtgca | attctagtca | aattattgcg | ttttttttacc | caaatgttta | atgtaaaact | 540 |
| gaaatttggc | acacttgcgc | aaatatatac | agggtatttt | gaaaaaatta | aacaggatga | 600 |
| taaaagttgc | acagaaactt | atctcaagat | ttacccgcag | aaagatgctt | naaaaattga | 660 |
| tatttgacag | agcaaaacct | gagattcacg | tcttttagtt | gtttgacttg | aaattttggt | 720 |
| gacaggtagg | tatcatgaaa | aacaaacaaa | acgtaaaaat | atcacgtgat | taaagtgtat | 780 |
| cttacagacc | agaaacagtt | ttattaactt | ctattattct | attttgcaat | atacacattg | 840 |
| tatcaatttc | ttgagttact | cgaagtaata | ccgacctatc | atcagaattt | caagtcaaca | 900 |
| caacattata | tggggctgat | tagggaatga | ttttgtctct | tttagatgct | ttcaagata | 960 |
| cccagatcat | atgaaacagc | atgacttttt | caagagtgcc | atgcccgaag | gttatgtaca | 1020 |
| ggaaagaact | atattttaca | aagatgacgg | gaactacaaa | tcacgtgctg | aagtcaagtt | 1080 |
| tgaaggtgat | accctcgtta | atagaattga | gttaaaaggt | attgatttta | agaagatgg | 1140 |
| aaacattctt | ggacacaaaa | tggaatacaa | ctataactca | cacaatgtat | acatcatggc | 1200 |
| agacaaacaa | aagaatggaa | tcaaagttaa | cttcaaaatt | gtatgtatac | gttaagggca | 1260 |
| taaattttg | cgggcataaa | atcttgcgaa | atttattatc | gcgaataggt | tacgcaaaat | 1320 |
| ctataattaa | aatgtatttt | tttctgctga | ttttctaaat | aacaactcaa | cccgtcattt | 1380 |
| ttatatcgca | aaaataaatt | ccgaaataat | ttatgctcgc | aaaaatttag | gcccataagt | 1440 |
| agacttttga | tatctgcgtg | ctctgcaatg | aagtaaaaat | acgatatttt | cattgaaata | 1500 |
| cacgggttca | agttatttg | ttaattcaat | aagcgtgcgc | agaaattaaa | ggacgtataa | 1560 |
| agatacgaac | acatcaaacc | attcatgcgt | aaataatgtt | ctattttaa | aattcaccaa | 1620 |
| agcttaaata | ttcttaagaa | ttattcatgt | gccatgggag | caacaatata | gttatggaca | 1680 |
| aaaatttctg | agttcacttt | tatttctgcg | cgcccgcatc | aaagttcaaa | caactgtgaa | 1740 |

```
cccgagtttt ttccagcttg caattttaat aagagacaaa aagcaaattg cagttcaaga    1800
aaatcgagat attgccagat gtaaacattt aataagagac aaaaagttca taagcgttct    1860
aaagaacagc aacaaaataa taattagaat taaacgagtt ctcaaacaaa ataaaaactg    1920
aagtcaaaga gtcagtaagg aatttagtta acgatgcttt ataatcaaag ttttaattcc    1980
agttcatgta tgcaattaac aataagatct tggagaattg aatatgtttc gaaattttat    2040
aaattcggat ttaatttcta aagttgtgta tcaaaaatag ttcaaactat tttcatgaaa    2100
agatgataaa ttacggtaat aagtatataa tataatcaat taaaattaat tttaggctca    2160
aattacagaa tccacgtttt ttttctctag acatagcaca gtgtttagat gtttgtttta    2220
tttcatccat ccttattaca gttttcctct gaactttaat actagcgtac aatttgaata    2280
ataatctgaa atgattcaac ttttcagaga cacaacattg aagatggaag cgttcaacta    2340
gcagaccatt atcaacaaaa tactccaatt ggcgatggcc ctgtcctttt accagacaac    2400
cattacctgt ccacacaatc tgcccttttcc aaagatccca acgaaaagag agatcacatg    2460
atccttcttg agtttgtaac agctgctggg attacacatg gcatggatga actatacaaa    2520
taaatgtcca gacttccaat tgacactaaa gtgtccgaac aattactaaa atctcagggt    2580
tcctggttaa attcaggctg agatattatt tatatattta tagattcatt aaaattttat    2640
gaataattta ttgatgttat taataggggt tattttctta ttaaataggc tactggagtg    2700
cattcctaat tctatattaa ttacaatttg atttgacttg ctcagaatcc cgcttcattg    2760
cttttccact tgcattatcc ttatttagta ttaatttgta ttttggtttg gctacattga    2820
gtgcaaaaaa cctaattttc ggacgaattt tcgaacgaat ttttttgacg gaattttctt    2880
cattctattt actcctctag ctaaattatt ttacctttt gttaatttgg ttaaattatt    2940
ctctgagccg atgattgaga aattaatgga ttaaaagtga gtaccttaca tgttgtcaac    3000
ttgtaacgaa tggaaaaaga aattacgttt caagagtttg aaaggtaata cagttacagt    3060
taaccgcaga aaaattgcat gatgattgat aaattcgatt tttgttatcc taaaattttc    3120
caaacgtcag tggccgacga ctttatcagg gacttctaaa agtgaaaaat aatcaggtgc    3180
ggatttcgaa ggcgcaaaac tataggaaga gagcgaaatg tcattaaatt atcatattct    3240
attaactgat gacaatagat gatgaaaagt ttatgattat tcactctcct cctgtaatta    3300
tgcgaccctt ctagattcac gcctgaaagt atagctacct gggatgaagt actagtctga    3360
ggactcttca cctaaaaatt aaattcttat aagagtaaac aagaaactta gcagttacaa    3420
acgggagagc gatgagaaac aaaaacaatt acgttgccac tatgaatatc gatgttcaat    3480
cattttgtt ccttacttat aagaacgaga tcgtcttaac ttaaaatagt aaaatgttat    3540
caagataata gcaattttt accgacacag cgaagactca ctactgaaat gatcagtttt    3600
aatcaggcaa ataatccgtg gcacataata gtgaccgaaa ataattaatc ggcattaaga    3660
ctaccgaaat aataatgttt tttctactgc gtatacgcgt gagaaatttt caataagctc    3720
atcatcttca gcatagttat acttttatgt aaagtatcaa ttccgacata aaataacggc    3780
ttattatcga aataatagcg ttttctctac tccatgcgcg tcaaaagttc tctctaggct    3840
catcatcttc agcataatta taattttgt aagtaccag ttccggtcga aaataatgac    3900
taattaccga aattatagtg tttttctatt gccatgcgcg tgaaaatttt tgattgaatc    3960
atcatcttca gcataggcat aattctttgt aaaatatcga ttccgacata aaataatggc    4020
ctattaccga aataatcgcg tttttcctac tgcgcatgcg cgtcaaaaat tatatttta    4080
ttcatcatct tcagcataat tatattttt tgtaaagtac cagttccggt agaaaataat    4140
```

-continued

```
gacttgttac tgaaataata gcgttttcct attgcgcatg cgctataaaa attaaagtaa    4200
cgtcatcata ttcagcatgg tattgaaatt ttcaaattta attaacctat tgaacaagaa    4260
tgtacacttg catcaaaata ggtgaaattc gccaatatcg ctaaatgtga cgcgcgggag    4320
caatactacg catgtagctt caggtaaagc atgtagaaac tcggaggagt aggagtccac    4380
cgtcgaaact aaaacgggat acactacgct atggccttcg ctctcccgta aaagggact    4440 aacaatacga cctaattgaa atactaaaaa aaacaagaga atttaaccc ctttgttaac    4500 acttttcaaa agtgggattt tttagccaac catctggtat atatggttgc tcattttatt    4560
attatctctt tctttattgt tggtacaacg tagtcaaaat acaaattagg ttaataaaaa    4620
gcaacattat aatgtataaa atctaattgt gtctaattac cgacaaattt tacaggaaca    4680
gttttcacca gaccgagtct taattttagt tttaaaagaa attatgtttc tactgttctg    4740
acaatctgaa gacaattagt tctagtgtaa caatgctctg aattgaatat attcagcaat    4800
attttgtttg taagaattgg atgaatgtac gaaccttcag cagatttata ccaagtgtta    4860
gatttaacaa gatttgcaag ctgatgagtt tcgagaaaat tcaacatatc tggatttgag    4920
ggtggaacat taaaatctcc taagataata attctatcat aattagaata taaattatca    4980
atgatgtcat ttaagtgatc tagaaaaata ttgatagtaa cagttggatg tttgtatata    5040
gaaatagtaa gccatctatt tttcccaaat gcgagttcaa aaaccaaaat tggattcctt    5100
caaagaaaaa agacattaag aaacttgatg gaatcccttc tcgactgtaa acaagcagtc    5160
tctgggatcc                                                           5170
```

<210> SEQ ID NO 9
<211> LENGTH: 966
<212> TYPE: DNA
<213> ORGANISM: Aequorea victoria

<400> SEQUENCE: 9

```
tacacacgaa taaagataa caaagatgag taaaggagaa gaacttttca ctggagttgt      60
cccaattctt gttgaattag atggtgatgt taatgggcac aaattttctg tcagtggaga    120
gggtgaaggt gatgcaacat acggaaaact tacccttaaa tttatttgca ctactggaaa    180
actacctgtt ccatggccaa cacttgtcac tactttctct tatggtgttc aatgcttttc    240
aagataccca gatcatatga acagcatga cttttttcaag agtgccatgc ccgaaggtta    300
tgtacaggaa agaactatat ttttcaaaga tgacgggaac tacaagacac gtgctgaagt    360
caagtttgaa ggtgataccc ttgttaatag aatcgagtta aaaggtattg attttaaaga    420
agatggaaac attcttggac acaaattgga atacaactat aactcacaca atgtatacat    480
catggcagac aaacaaaaga atggaatcaa agttaacttc aaaattagac acaacattga    540
agatggaagc gttcaactag cagaccatta tcaacaaaat actccaattg gcgatggccc    600 tgtccttta ccagacaacc attacctgtc cacacaatct gccctttcga agatcccaa    660 cgaaaagaga gaccacatgg tccttcttga gtttgtaaca gctgctggga ttacacatgg    720
catggatgaa ctatacaaat aaatgtccag acttccaatt gacactaaag tgtccgaaca    780
attactaaaa tctcagggtt cctggttaaa ttcaggctga gatattattt atatatttat    840
agattcatta aaattgtatg aataatttat tgatgttatt gatagaggtt attttcttat    900
taaacaggct acttggagtg tattcttaat tctatattaa ttacaatttg atttgacttg    960
ctcaaa                                                              966
```

```
<210> SEQ ID NO 10
<211> LENGTH: 35
<212> TYPE: DNA
<213> ORGANISM: Artificial Sequence
<220> FEATURE:
<223> OTHER INFORMATION: Synthetic Construct

<400> SEQUENCE: 10
taatacgact cactatagga aagagagttt caacg                                  35

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
ggccatggag tggtaccttc                                                   20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
gaaggtacca ctccatggcc                                                   20

<210> SEQ ID NO 13
<211> LENGTH: 30
<212> TYPE: DNA
<213> ORGANISM: Artificial Sequence
<220> FEATURE:
<223> OTHER INFORMATION: Synthetic Construct

<400> SEQUENCE: 13
aaagcttctg caggggggccc cctgggggc                                        30
```